US010677904B2

(12) United States Patent
Saitou et al.

(10) Patent No.: US 10,677,904 B2
(45) Date of Patent: Jun. 9, 2020

(54) OBJECT DETECTION APPARATUS

(71) Applicant: DENSO CORPORATION, Kariya, Aichi-pref. (JP)

(72) Inventors: Takashi Saitou, Nishio (JP); Yuuji Kakuya, Nishio (JP); Takahisa Matsumoto, Kariya (JP)

(73) Assignee: DENSO CORPORATION, Kariya, Aichi-pref. (JP)

( * ) Notice: Subject to any disclaimer, the term of this patent is extended or adjusted under 35 U.S.C. 154(b) by 255 days.

(21) Appl. No.: 15/561,352

(22) PCT Filed: Mar. 15, 2016

(86) PCT No.: PCT/JP2016/001477
§ 371 (c)(1),
(2) Date: Sep. 25, 2017

(87) PCT Pub. No.: WO2016/157779
PCT Pub. Date: Oct. 6, 2016

(65) Prior Publication Data
US 2018/0081048 A1 Mar. 22, 2018

(30) Foreign Application Priority Data
Mar. 27, 2015 (JP) ................................. 2015-066752

(51) Int. Cl.
G01S 13/04 (2006.01)
A61B 5/00 (2006.01)
(Continued)

(52) U.S. Cl.
CPC ................ *G01S 13/04* (2013.01); *A61B 5/05* (2013.01); *A61B 5/6893* (2013.01);
(Continued)

(58) Field of Classification Search
CPC ........ G01S 13/04; G01S 13/56; G01S 13/003; G01S 13/46; A61B 5/6893; A61B 5/05;
(Continued)

(56) References Cited

U.S. PATENT DOCUMENTS

2008/0002753 A1* 1/2008 Timans ................ G01K 11/125
374/2
2009/0079563 A1* 3/2009 Tsuji ........................ G01S 13/04
340/552
2014/0015706 A1* 1/2014 Ishihara ................ G08B 21/22
342/27

FOREIGN PATENT DOCUMENTS

JP H09228679 A 9/1997
JP 2008151510 A 7/2008
(Continued)

Primary Examiner — Bo Fan
(74) Attorney, Agent, or Firm — Harness, Dickey & Pierce, P.L.C.

(57) ABSTRACT

An object detection apparatus includes: a transmitter transmitting a radio wave with a predetermined intensity at the radio wave transmission end; a receiver receiving the radio wave, which is to be transmitted when the radio wave is transmitted from the transmitter, at the radio wave reception end; a setter setting a transmission scheme of the transmitter to a plurality of different transmission characteristics; a transmission controller controlling the transmitter to transmit the radio wave with the transmission scheme, which is to be set when the setter sets the transmission scheme; and a detector detecting a presence of the object at a position inside the vehicle, based on a detected reception intensity indicating a respective radio wave reception intensity received by the receiver, the object blocking the radio wave transmitted from the transmitter to the receiver at the position inside the vehicle.

11 Claims, 9 Drawing Sheets

(51) Int. Cl.
    *G01V 3/12*     (2006.01)
    *G08B 13/187*     (2006.01)
    *H04W 64/00*     (2009.01)
    *G08B 21/24*     (2006.01)
    *H04W 4/40*     (2018.01)
    *G08B 21/22*     (2006.01)
    *G01S 13/00*     (2006.01)
    *G01S 13/46*     (2006.01)
    *G01S 13/56*     (2006.01)
    *G08B 13/22*     (2006.01)
    *A61B 5/05*     (2006.01)
    *H04W 4/48*     (2018.01)

(52) U.S. Cl.
    CPC ............ *G01S 13/003* (2013.01); *G01S 13/46* (2013.01); *G01S 13/56* (2013.01); *G01V 3/12* (2013.01); *G08B 13/187* (2013.01); *G08B 13/22* (2013.01); *G08B 21/22* (2013.01); *G08B 21/24* (2013.01); *H04W 4/40* (2018.02); *H04W 64/00* (2013.01); *H04W 4/48* (2018.02)

(58) Field of Classification Search
    CPC ...... G08B 21/24; G08B 21/22; G08B 13/187; G08B 13/22; G01V 3/12; H04W 4/48; H04W 4/40; H04W 64/00
    USPC .......................................................... 342/27
    See application file for complete search history.

(56) References Cited

FOREIGN PATENT DOCUMENTS

| | | |
|---|---|---|
| JP | 2010249646 A | 11/2010 |
| JP | 2015041332 A | 3/2015 |
| WO | WO-2012137285 A1 | 10/2012 |

\* cited by examiner

FIG. 4

| COUNTER C VALUE | FIRST DETECTION TRANSMISSION ANTENNA | SECOND DETECTION TRANSMISSION ANTENNA |
|---|---|---|
| 1 | 0 | 10 |
| 2 | 1 | 9 |
| 3 | 2 | 8 |
| 4 | 3 | 7 |
| ... | ... | ... |
| 10 | 9 | 1 |
| 11 | 10 | 0 |

Cs TYPE (Cs=11) { (rows 1 through 11)

(a) BEFORE SEAT ARRANGEMENT (b) AFTER SEAT ARRANGEMENT (a) AFTER SEAT ARRANGEMENT (WITHOUT PERSON)

(b) AFTER SEAT ARRANGEMENT (WITH PERSON)

OBJECT DETECTION APPARATUS

CROSS REFERENCE TO RELATED APPLICATIONS

This application is a U.S. National Phase Application under 35 U.S.C. 371 of International Application No. PCT/JP2016/001477 filed on Mar. 15, 2016 and published in Japanese as WO 2016/157779 A1 on Oct. 6, 2016. This application is based on and claims the benefit of priority from Japanese Patent Application No. 2015-066752 filed on Mar. 27, 2015. The entire disclosures of all of the above applications are incorporated herein by reference.

TECHNICAL FIELD

The present disclosure relates to a technique for detecting an object in a vehicle.

BACKGROUND ART

There is known a conventional technique that detects an object such as a person or item in a vehicle. Patent Literature 1 proposes a technique that transmits a microwave toward a vehicle in a parking lot, receives a reflected wave reflected from inside the vehicle by a device provided in the parking lot, and detects the presence or absence of a person inside the vehicle on the basis of the reflected wave being received.

However, a portion of the transmitted radio wave reflected from a human body inside the vehicle is smaller than a portion of the transmitted radio wave absorbed by the human body. That is, the above technique detects the presence or absence of an object inside the vehicle on the basis of the reflected wave with weak radio wave intensity, and can thus have reduced detection accuracy.

PRIOR ART LITERATURES

Patent Literature

Patent Literature 1: JP H09-228679 A

SUMMARY OF INVENTION

It is an object of the present disclosure to provide a technique that improves the accuracy of detecting an object inside a vehicle.

An object detection apparatus according to an aspect of the present disclosure is mounted to a vehicle, and detects a predetermined object between a radio wave transmission end and a radio wave reception end. The object detection apparatus includes: a transmitter that transmits a radio wave, which has a predetermined intensity, at the radio wave transmission end; a receiver that receives the radio wave, which is configured to be transmitted when the radio wave is transmitted from the transmitter, at the radio wave reception end; a setter that sets a transmission scheme of the transmitter to a plurality of different transmission characteristics; a transmission controller that controls the transmitter to transmit the radio wave with the transmission scheme having the plurality of different transmission characteristics, which is configured to be set when the setter sets the transmission scheme; and a detector that detects a presence of the object at a position inside the vehicle, based on a detected reception intensity indicating a respective radio wave reception intensity received by the receiver, the object blocking the radio wave having the plurality of different transmission characteristics transmitted from the transmitter to the receiver at the position inside the vehicle.

The object detection apparatus according to the present disclosure including such a configuration determines the presence or absence of an object between the receiving end and the transmitting end of the radio wave on the basis of absorption of the radio wave by the object. The portion of the radio wave absorbed by the object is larger than the portion of the radio wave being reflected, so that a difference in the reception intensity between when an object is present and when no object is present between the receiving end and the transmitting end of the radio wave is larger than that of a conventional technique using reflected waves. The object detection apparatus of the present disclosure also transmits the radio wave with the plurality of transmission characteristics and detects the presence of an object on the basis of the reception intensities of the waves. This can prevent false detection indicating the presence of an object when no object is present because, even when there occurs a situation where the reception intensity has a value near zero in the absence of an object with a certain transmission characteristic, the reception intensity having a certain value can be obtained with another transmission characteristic. The present disclosure can thus improve the accuracy of detecting an object.

BRIEF DESCRIPTION OF DRAWINGS

The above and other objects, features and advantages of the present disclosure will become more apparent from the following detailed description made with reference to the accompanying drawings. In the drawings:

FIG. 4 is a diagram illustrating an example of a distribution ratio table;

EMBODIMENTS FOR CARRYING OUT INVENTION

Embodiments to which the present disclosure is applied will now be described with reference to the drawings.

1. First Embodiment

Figure 1:
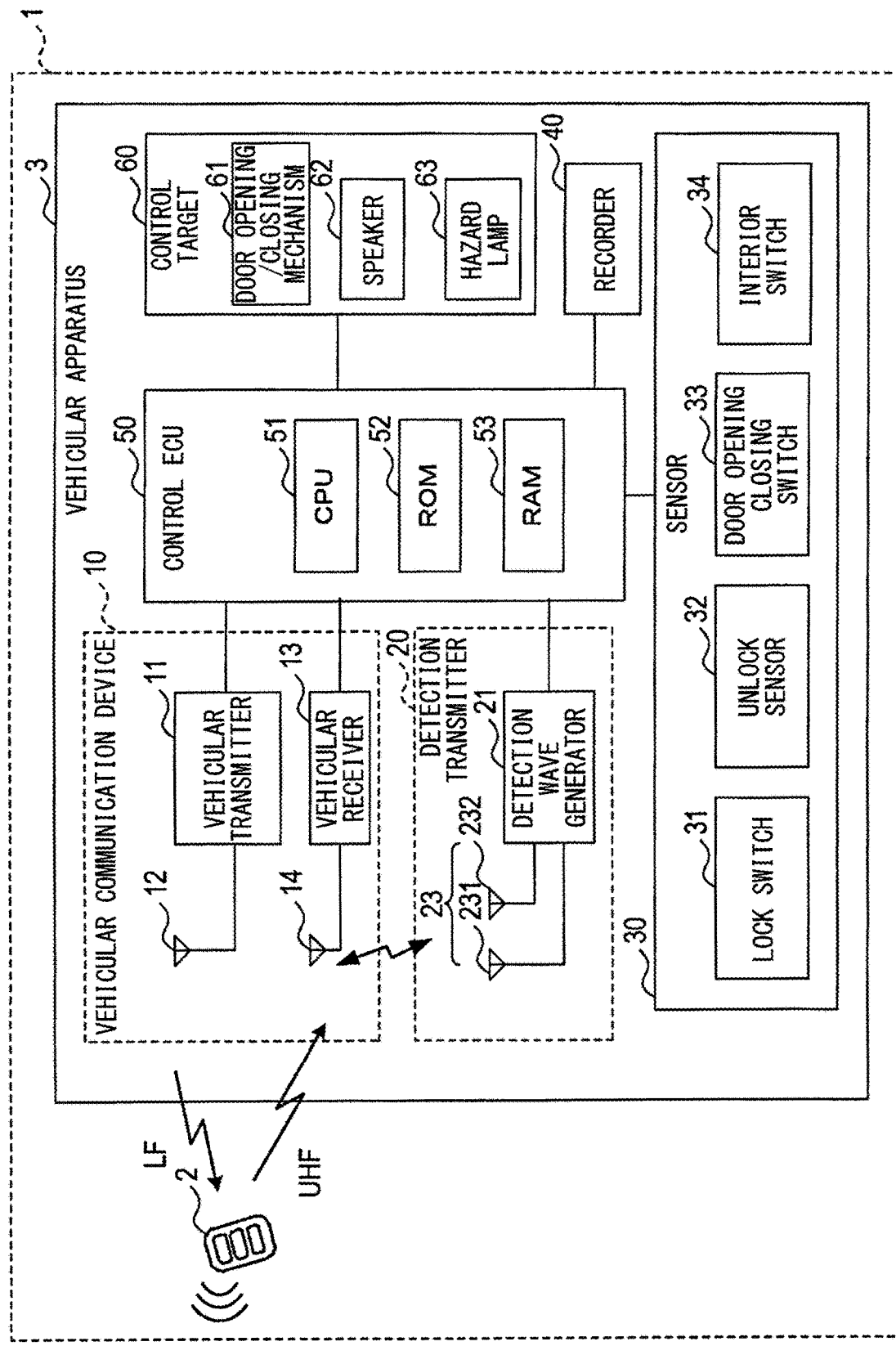
FIG. 1 is a block diagram illustrating the configuration of a vehicular device and a smart system according to a first embodiment.

FIG. 1 is a block diagram illustrating the configuration of a communication system 1 according to an embodiment to which the present disclosure is applied. The communication system 1 is a so-called smart system that performs predetermined control on a vehicle by a mobile terminal possessed by a user, and includes a vehicular device 3 mounted in a vehicle (automobile) and a mobile terminal (an electronic key) 2 possessed by a driver or the like who is a user of the vehicle. The electronic key 2 performs at least one of locking and unlocking a door of the vehicle and starting an engine by communicating with the vehicular device 3, and is configured as a wireless device that exchanges data with the vehicular device 3. Wireless communication from the electronic key 2 to the vehicular device 3 is performed by using radio waves in the UHF band (300 MHz to 400 MHz band), and wireless transmission from the vehicular device 3 to the electronic key 2 is performed by using radio waves in the LF band (approximately 100 KHz)). Data transmitted from the electronic key 2 to the vehicular device 3 includes an authentication code used to identify the electronic key 2.

As illustrated in FIG. 1, the vehicular device 3 includes an vehicular communication device 10, a detection transmission unit 20, a sensor 30, a control ECU 50, a control target 60, and a recorder 40. The ECU is an abbreviation for electronic control unit. The vehicular device 3 is configured to receive power supply even when an ignition switch of the vehicle is turned off.

The vehicular communication device 10 includes an vehicular transmitter 11, an vehicular transmission antenna 12, an vehicular receiver 13, and an vehicular reception antenna 14. The vehicular transmitter 11 modulates a transmission carrier wave in a predetermined frequency band (the LF band such as one hundred and several tens KHz band) with respect to output data that is output from the control ECU 50, thereby generating a transmission signal transmitted to the electronic key 2. The vehicular transmitter 11 causes the vehicular transmission antenna 12 to transmit the transmission signal being generated.

The vehicular reception antenna 14 receives a radio wave in a predetermined frequency band (the UHF band (300 MHz to 400 MHz band)) transmitted from the electronic key 2 or the detection transmission unit 20. In the present embodiment, the vehicular reception antenna 14 is provided on a C-pillar behind a back seat. The vehicular receiver 13 demodulates data from a received signal received by the vehicular reception antenna 14, and inputs the demodulated data to the control ECU 50. The vehicular receiver 13 further generates a reception intensity signal representing the intensity of the received signal received by the vehicular reception antenna 14 as an analog signal such as a voltage value, and inputs the reception intensity signal to the control ECU 50.

Figure 2:
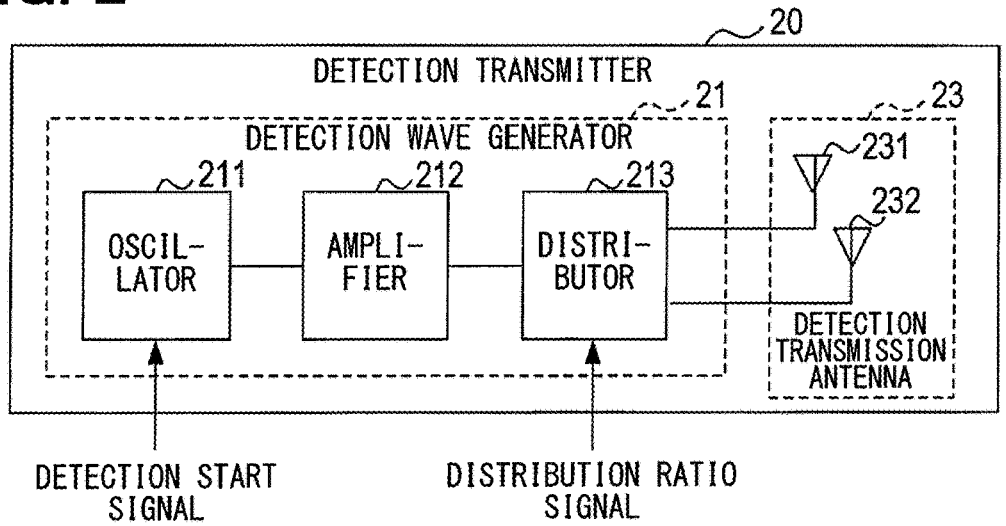
FIG. 2 is a block diagram illustrating the configuration of a detection transmission unit.

As illustrated in FIG. 2, the detection transmission unit 20 includes a detection wave generator 21 and a detection transmission antenna 23. The detection transmission antenna 23 includes a first detection transmission antenna 231 and a second detection transmission antenna 232. The first detection transmission antenna 231 includes a dipole antenna that transmits vertically polarized radio waves, and the second detection transmission antenna 232 includes a dipole antenna that transmits horizontally polarized radio waves.

The detection wave generator 21 includes an oscillator 211, an amplifier 212, and a distributor 213. The oscillator 211 generates a detection carrier signal in the UHF band (300 MHz to 400 MHz band). Upon receiving input of a detection start signal from the control ECU 50, the oscillator 211 supplies the detection carrier signal that is unmodulated to the amplifier 212 for a predetermined detection transmission period.

The amplifier 212 amplifies the unmodulated detection carrier signal to have predetermined detection transmission power, and supplies the signal to the distributor 213. The distributor 213 distributes the detection carrier signal to the first detection transmission antenna 231 and the second detection transmission antenna 232, each of which transmits the signal as a detection transmission wave. The distributor 213 is configured to adjust a distribution ratio of detection transmission power to the first detection transmission antenna 231 and the second detection transmission antenna 232 according to a distribution ratio signal from the control ECU 50.

The detection transmission antenna 23 transmits only the vertically polarized radio waves when the distribution ratio (the first detection transmission antenna 231:the second detection transmission antenna 232) is 10:0 with 10 being the total detection transmission power, for example. The detection transmission antenna 23 transmits only the horizontally polarized radio waves when the distribution ratio is 0:10, for example. When the distribution ratio is changed at a predetermined rate to be 0:10, 1:9, 2:8, . . . 10:0, for example, the radio waves transmitted from the first detection transmission antenna 231 and the second detection transmission antenna 232 are synthesized so that the detection transmission antenna 23 can transmit circularly polarized waves. Such a change in the distribution ratio causes a change in directivity of the detection transmission antenna 23 in response to the change.

Figure 3:
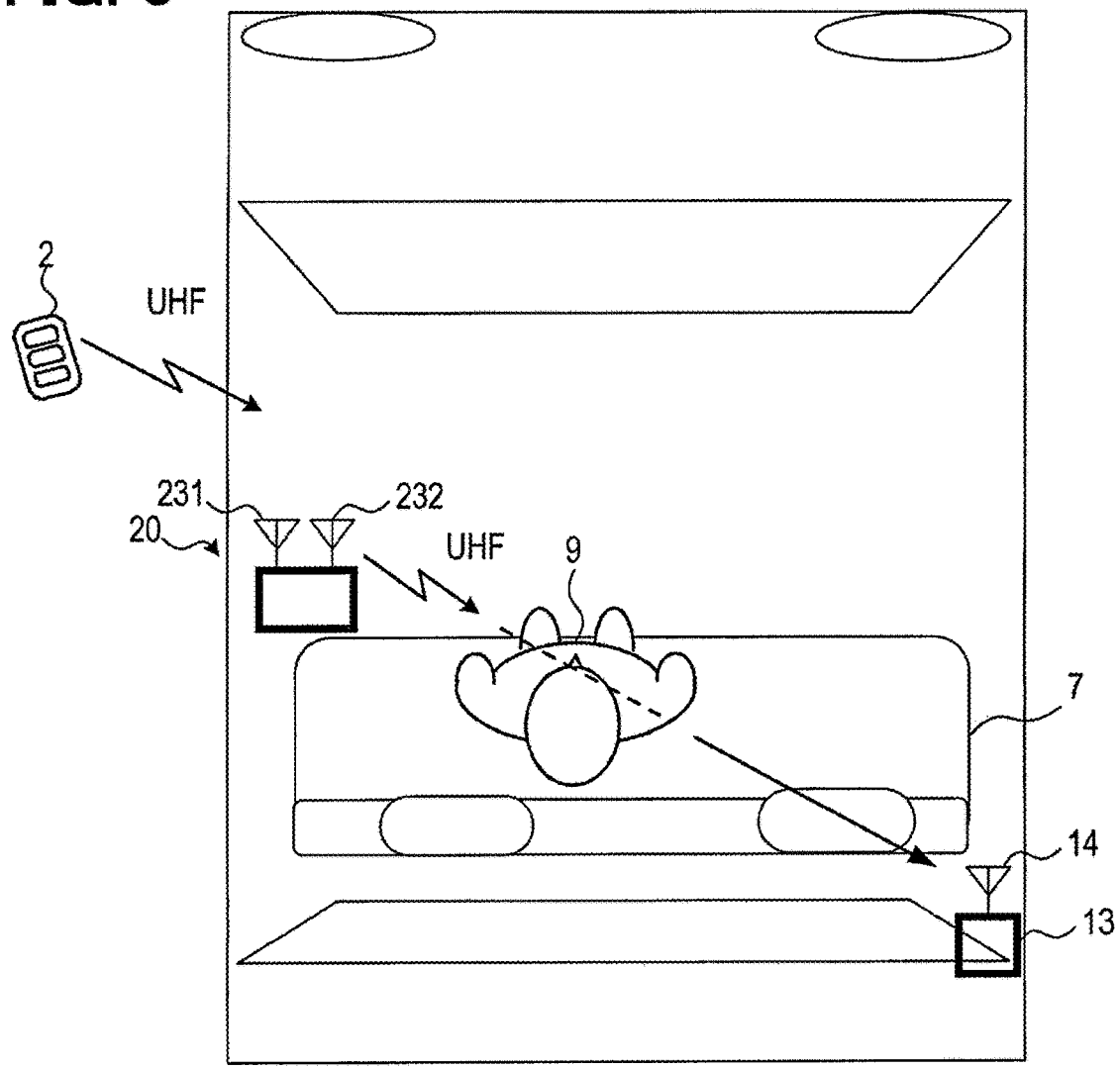
FIG. 3 is a diagram illustrating an example of the arrangement of the detection transmission unit and a vehicular receiver.

As illustrated in FIG. 3, in the present embodiment, the detection transmission unit 20 (at least the first detection transmission antenna 231 and the second detection transmission antenna 232) is installed on the vehicle floor of the back seat 7 on the side of a passenger seat. That is, the detection transmission unit 20 is disposed such that the detection transmission wave transmitted from a transmitting end being the detection transmission unit 20 to a receiving end being the vehicular receiver 13 is blocked by an object in the back seat 7 of the vehicle. An example of the object is a person 9 in the back seat 7.

Returning to FIG. 1, the description will be continued. The recorder 40 is a rewritable recording device such as an EEPROM or a flash ROM. The distribution ratio between the first detection transmission antenna 231 and the second detection transmission antenna 232 is recorded in advance. In the present embodiment, the distribution ratio is recorded in a table format as illustrated in an example of FIG. 4. A distribution ratio table illustrated in FIG. 4 records a plurality of types of distribution ratios such as 0:10, 1:9, 2:8, . . . 10:0 with 10 representing the detection transmission power.

Returning to FIG. 1, the description will be continued. The sensor 30 detects that a passenger door of the vehicle is operated by a user. Here, there will be described an example where the sensor 30 detects an operation on a passenger door on the side of a driver's seat. The sensor 30 includes a lock switch 31, an unlock sensor 32, a door opening/closing switch 33, and an interior switch 34. The lock switch 31 and the unlock sensor 32 are provided on a door handle (outside the vehicle interior) of the passenger door on the side of the driver's seat. The lock switch 31 detects a pressing operation by a person and outputs a detected signal to the control ECU 50. The unlock sensor 32 detects a touch by a person and outputs a detected signal to the control ECU 50. The door opening/closing switch 33 detects opening of the passenger door on the side of the driver's seat, and detects a detected signal to the control ECU 50. The interior switch 34 is provided on the door handle (inside the vehicle interior) of the passenger door on the side of the driver's seat, detects an unlocking operation or a locking operation performed on the door from inside the vehicle interior, and outputs a detected signal to the control ECU 50. The lock switch 31, the unlock sensor 32, the door opening/closing switch 33, and the interior switch 34 are provided on each passenger door.

The control ECU 50 is an electronic control unit equipped with a microcomputer including a CPU 51, a ROM 52, a RAM 53, and the like. The ROM 52 records the authentication code used to identify the electronic key 2 that is registered in advance in the vehicle. The electronic key 2 registered in advance in the vehicle will be hereinafter referred to as a registered key. The CPU 51 executes at least object detection processing and locking/unlocking processing according to a program stored in the ROM 52.

The object detection processing will be described later. Where various processing can be thought of as the locking/unlocking processing, one example will be briefly described. The locking/unlocking processing confirms, for example, that the electronic key 2 carried by a user approaching the vehicle being parked from outside the vehicle is the registered key on the basis of the authentication code included in data received from the electronic key 2, and thereafter sets a body ECU (to be described) to an unlock standby state. The locking/unlocking processing also confirms that the electronic key 2 carried by a user who gets off the vehicle upon parking the vehicle is the registered key on the basis of the authentication code, and thereafter sets the body ECU to a lock standby state, for example.

The control target 60 includes a plurality of devices for controlling the behavior of a control target in the vehicle. An example of such devices is the body ECU described later. The control target includes at least a door opening/closing mechanism 61, a speaker 62, a hazard lamp 63, and the like. The door opening/closing mechanism 61 is an actuator that opens/closes the passenger door on the side of the driver's seat, the speaker 62 generates a warning sound toward the outside of the vehicle in response to a command from the control ECU 50, and the hazard lamp 63 issues a warning to the outside of the vehicle by blinking repeatedly in response to a command from the control ECU 50.

In the unlock standby state, the body ECU (not shown) actuates the door opening/closing mechanism 61 and automatically unlocks the passenger door on the side of the driver's seat upon receiving a detected signal from the unlock sensor 32. In the lock standby state, the body ECU actuates the door opening/closing mechanism 61 and automatically locks the passenger door on the side of the driver's seat upon receiving a detected signal from the lock switch 31. That is, in the communication system 1, carrying of the electronic key 2 allows a user to automatically lock and unlock the passenger door on the side of the driver's seat without performing any special operation.

[1-2. Processing]

Next, the object detection processing executed by the CPU 51 of the control ECU 50 will be described with reference to a flowchart illustrated in FIG. 5. The object detection processing is executed in response to locking of all passenger doors when the vehicle is parked. It is assumed that the engine is stopped when the vehicle is parked. In the following description, the control ECU 50 is the subject of a sentence where it is omitted.

In S110, a counter C is reset. Specifically, a zero is assigned to the counter C. In S120, the value of the counter C is incremented by one. Then in S130, a transmission characteristic of the detection transmission antenna 23 is set. That is, the control ECU sets the distribution ratio when the detection transmission wave is transmitted from a detection transmission antenna 231 and the second detection transmission antenna 232. More specifically, the control ECU reads a distribution ratio corresponding to the value of the counter C from the recorder 40, and outputs a distribution ratio signal representing the distribution ratio. A distribution ratio signal representing the distribution ratio of 0:10 is output when one is set as the value of the counter C, for example.

In S140, the detection transmission wave is transmitted from the detection transmission antenna 23 (the first detection transmission antenna 231 and the second detection transmission antenna 232). More specifically, the detection start signal is output.

Then in S150, the control ECU stands by until a radio wave in some UHF band is received by the vehicular reception antenna 14 and the received signal is input to the vehicular receiver 13. Once the received signal is input to the vehicular receiver 13, the control ECU determines in S160 whether the received signal being input is based on the transmission detection wave from the detection transmission unit 20. Specifically, it is determined that the received signal being input is based on the transmission detection wave from the detection transmission unit 20 when received data demodulated by the vehicular receiver 13 on the basis of the received signal being input does not include the authentication code. If the received signal is not based on the detection transmission wave (NO in S160), it is determined that the received signal being input is based on the radio wave transmitted from the electronic key 2, whereby the present object detection processing is completed. On the other hand, the processing proceeds to S170 if the received signal being input is based on the detection transmission wave (YES in S160).

In S170, a reception intensity value of the received signal is specified on the basis of the reception intensity signal from the vehicular receiver 13 and is recorded in the RAM 53. In S180, the control ECU determines whether the detection transmission wave has been transmitted for all types of the distribution ratios prepared in advance in the distribution ratio table. With Cs being the number of types of the distribution ratios, it is determined that the detection transmission wave has been transmitted for all types of the distribution ratios when the value of the counter C is larger than or equal to a predetermined detection count Cs. The Cs is set to 11 in the example of FIG. 5. The processing proceeds to S120 to repeat the processing from S120 to S180 if the detection transmission wave has not been transmitted for all types of the distribution ratios. On the contrary, the processing proceeds to S190 if the detection transmission wave has been transmitted for all types of the distribution ratios.

In S190, the control ECU calculates an average value of the reception intensity values recorded for each distribution ratio in the RAM 53. In S200, it is determined whether a person is present in the vehicle. Specifically, it is determined that a person is present in the back seat 7 of the vehicle if the average value calculated in S190 is smaller than a predetermined first threshold recorded in advance in the ROM 52 (if the average value<the first threshold). The first threshold is set on the basis of the average value calculated in advance in S190 when there is no obstruction to the radio wave between the detection transmission antenna 23 and the vehicular reception antenna 14. The first threshold is recorded in advance in the ROM 52. The present object detection processing is completed if it is determined that no person is present in the vehicle (NO in S200). On the contrary, the processing proceeds to S210 if it is determined that a person is present (YES in S200).

In S210, a notification is provided in a first mode. Specifically, in the first mode, the speaker 62 outputs a warning sound to the outside of the vehicle and notifies the outside of the vehicle that a passenger is left in the back seat 7 of the vehicle.

The object detection processing causes the detection transmission antenna 23 to transmit the detection transmission wave with the plurality of different transmission characteristics (distribution ratios). It is then determined that a person is present between the detection transmission antenna 23 and the vehicular reception antenna 14 on the basis of the average value of the reception intensity values.

[1-3. Effects]

The following effects can be obtained according to the first embodiment detailed above.

[1A] The presence or absence of a person between the receiving end (vehicular reception antenna 14) and the transmitting end (detection transmission antenna 23) of the detection transmission wave is determined on the basis of absorption of the detection transmission wave by a person. The portion of the detection transmission wave absorbed by a person is larger than the portion of the wave being reflected. For this reason, a difference in the reception intensity between when a person is present between the receiving end and the transmitting end of the detection transmission wave and when a person is not present therebetween is detected with a larger value than that of a conventional technique using a reflected wave. The present embodiment can thus have higher accuracy of detecting a person than the conventional technique.

[1B] Depending on the state of propagation of radio waves in the vehicle, the reception intensity on the vehicular receiver 13 can be near zero smaller than the first threshold even when a person is not present at the time of transmitting the detection transmission wave from the detection transmission antenna 23 with a certain transmission characteristic. In other words, there is a possibility of false detection indicating the presence of a person even though the person is not in reality, when a determination is made on the basis of the reception intensity with such one transmission characteristic.

On the other hand, the present embodiment causes the detection transmission antenna 23 to transmit the detection transmission wave with the plurality of different transmission characteristics. On the basis of the average value of these reception intensities, a person is determined to be present at a position in the vehicle where the person blocks the detection transmission wave transmitted from the detection transmission antenna 23 to the vehicular reception antenna 14. As a result, the reception intensity in the absence of a person may be near zero with one transmission characteristic but is highly likely to be relatively strong with another transmission characteristic, whereby the average value of the plurality of reception intensities (detected reception intensities) exceeds the first threshold. That is, the present embodiment can prevent the false detection indicating the presence of a person even though the person is not present in reality.

Figure 6:
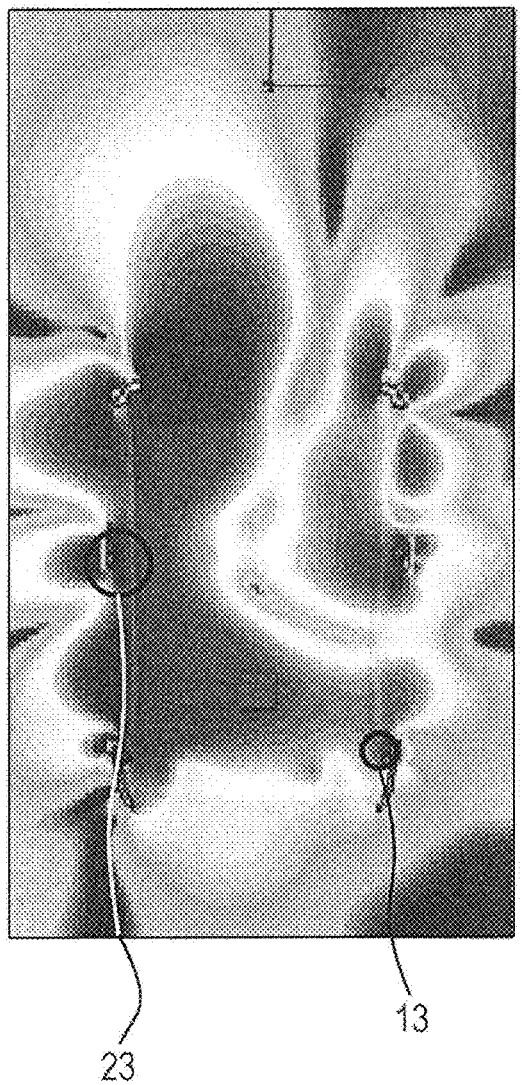
FIG. 6 illustrates an example of a simulation of a reception intensity distribution of a transmission detection wave in a vehicle interior in which no person is present, where (a) illustrates a situation before seat arrangement, and (b) illustrates a situation after the seat arrangement.
Figure 6:
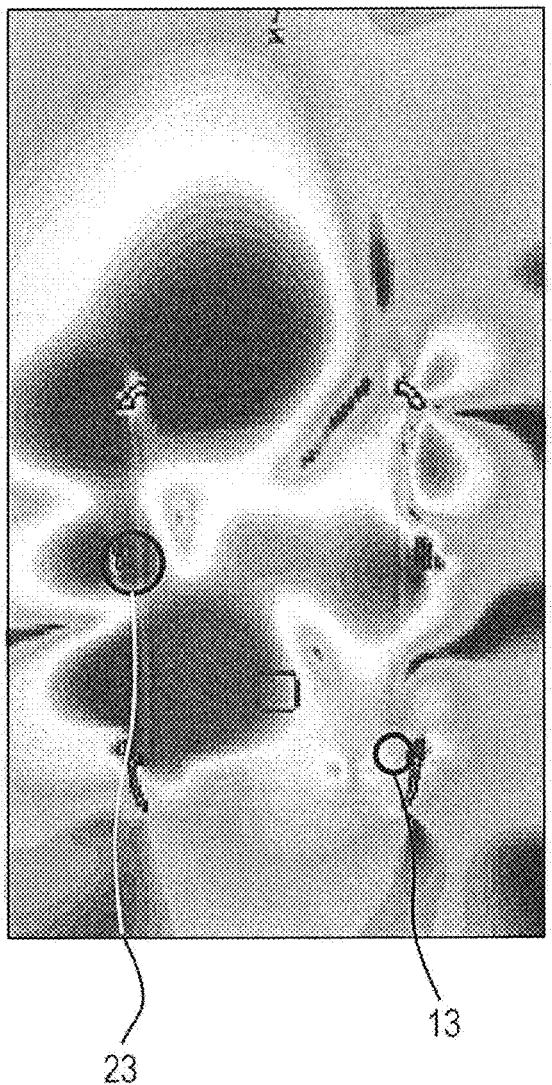

The aforementioned situation where the reception intensity equals zero can occur when seat arrangement such as moving of the driver's seat or passenger seat is performed in the vehicle interior, for example. This is because the state of propagation of the detection transmission wave in the vehicle changes due to the influence of the reflection of radio waves by the driver's seat or passenger seat after the seat is moved by the seat arrangement. The (a) and (b) of FIG. 6 are simulation diagrams each illustrating an example of the reception intensity distribution of the transmission detection wave in the vehicle interior in which no person is present with the detection transmission antenna 23 having a certain transmission characteristic. The reception intensity of a certain value is detected by the vehicular receiver 13 before the seat arrangement (the (a) of FIG. 6), whereas the reception intensity is near zero after the seat arrangement (the (b) of FIG. 6) in spite of the absence of a person.

Figure 7:
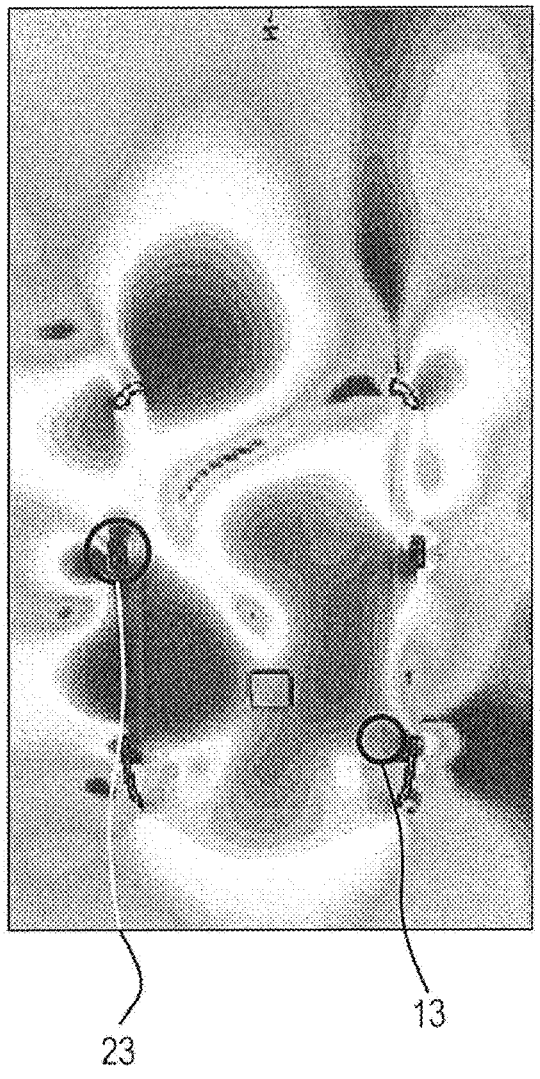
FIG. 7 illustrates an example of a simulation of the reception intensity distribution of the transmission detection wave in the vehicle interior after the seat arrangement, where (a) illustrates a situation when no person is present in the vehicle interior, and (b) illustrates a situation when a person is present in the vehicle interior.
Figure 7:
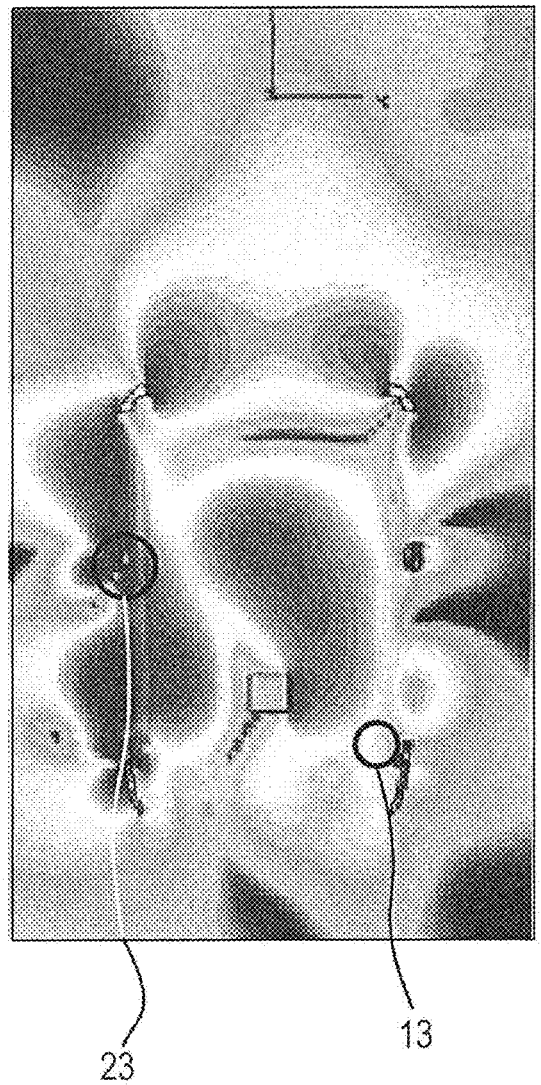

On the other hand, the (a) of FIG. 7 is a simulation diagram illustrating the distribution of the average value of the detected reception intensities according to the present embodiment in the vehicle interior with the absence of a person after the seat arrangement similar to that in FIG. 6B. It is confirmed that a value exceeding the first threshold is detected as the average value by the vehicular receiver 13. The (b) of FIG. 7 is a simulation diagram illustrating the distribution of the average value of the detected reception intensities in the vehicle interior with the presence of a person after the seat arrangement similar to that in the (a) of FIG. 7. It is confirmed that a value near zero and smaller than the first threshold is detected as the average value by the vehicular receiver 13.

[1C] The speaker 62 notifies the outside of the vehicle when the presence of a person in the vehicle is detected after all the passenger doors are locked at the time of parking of the vehicle. This allows the outside of the vehicle to be notified of a passenger left in the vehicle.

[1D] The detection transmission wave for detecting the presence of a person in the back seat 7 of the vehicle is received by the vehicular receiver 13 which is used to communicate with the electronic key 2 in the communication system 1. The vehicular receiver 13 that is a device on the receiving end in the communication system 1 doubles as a device that receives the detection transmission wave without individually including a device that receives the detection transmission wave, whereby the vehicular device 3 can be reduced in size and weight.

In the first embodiment, the vehicular device 3 corresponds to an example of the object detection apparatus, the detection transmission unit 20 corresponds to an example of a transmitter, the vehicular receiver 13 corresponds to an example of a receiver, and the control ECU 50 corresponds to an example of a setter, a transmission controller, a detector, and an alarm. The detection transmission antenna 23 corresponds to an example of a transmission antenna, and the speaker 62 corresponds to an example of a notification unit. Moreover, S130 corresponds to an example of the processing performed by the setter. Step S140 corresponds to an example of the processing performed by the transmission controller, S200 corresponds to an example of the processing performed by the detector, and S210 corresponds to an example of the processing performed by the alarm.

2. Second Embodiment

[2-1. Configuration]

Since the basic configuration of a second embodiment is similar to that of the first embodiment, a configuration different from the first embodiment will mainly be described while omitting a description of the configuration common to both embodiments.

The second embodiment is different from the first embodiment in that the detected result of the object detection processing in the first embodiment is applied to theft notification processing to be described later. Specifically, the present embodiment is different from the first embodiment in that the theft notification processing and the object detection processing are executed in parallel. The object detection processing executed by a control ECU 50 of the present embodiment is different from the object detection processing of the first embodiment illustrated in FIG. 5 in that S100 is added and S210 is replaced with S220.

[2-2. Processing]

[2-2-1. Object Detection Processing]

Figure 8:
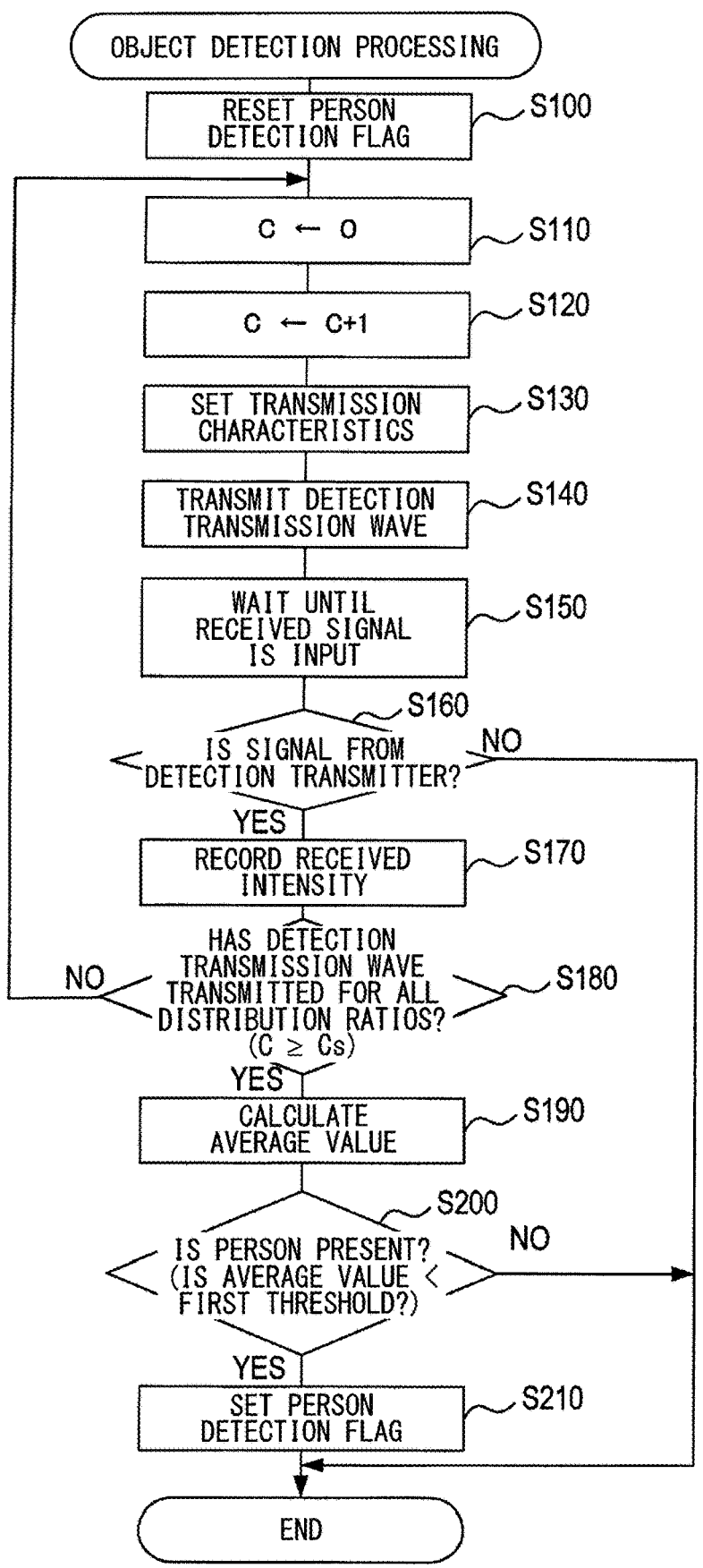
FIG. 8 is a flowchart of object detection processing according to a second embodiment.

The object detection processing executed by a CPU 51 of the control ECU 50 according to the present embodiment will be described with reference to a flowchart illustrated in FIG. 8.

In S100, a person detection flag is reset. Specifically, the person detection flag indicates that a person is present in a back seat 7 of the vehicle when being set, whereas that a person is not present in the back seat 7 of the vehicle when being reset. It is assumed, for example, that the person detection flag is set when the value of the person detection flag is one, and that the person detection flag is reset when the value is zero.

In each of steps S110 to S210, the processing similar to that of the first embodiment is executed. Note that if it is determined in S200 that a person is present in the back seat 7 of the vehicle (YES in S200), the processing proceeds to S220.

In S220, the person detection flag is set, and the present object detection processing is completed. That is, if it is determined that a person is present in the back seat 7 of the vehicle (YES in S200), the present object detection processing sets the person detection flag instead of notifying the outside of the vehicle as in the first embodiment.

[2-2-2. Theft Notification Processing]

The overview of the theft notification processing given as an example in the present embodiment will be described. Suppose that a driver locks all passenger doors upon parking the vehicle and leaves the vehicle, for example. If a suspicious person is hiding in the vehicle at this time without being noticed by the driver, the vehicle can be stolen by the suspicious person. The theft notification processing is carried out that prevents the vehicle from being stolen by such a suspicious person hiding in the vehicle.

Figure 9:
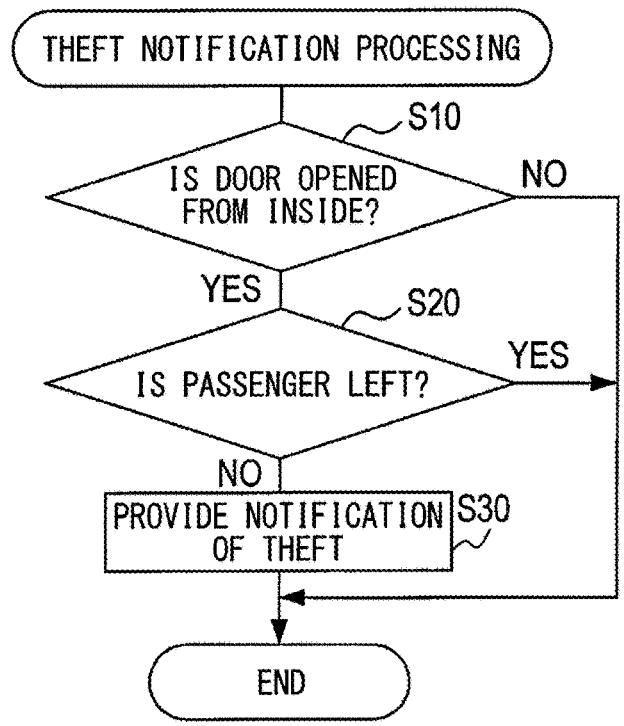
FIG. 9 is a flowchart of anti-theft processing.

The theft notification processing is executed by the CPU 51 in the control ECU 50 concurrently with the object detection processing according to a program recorded in a ROM 52. The theft notification processing is executed repeatedly at predetermined intervals with all the passenger doors being locked at the time of parking of the vehicle. The theft notification processing will be described with reference to a flowchart in FIG. 9.

In step (S) 10, it is determined whether any of the passenger doors is opened from inside the vehicle. The present theft notification processing is completed if it is determined that none of the passenger doors is opened from inside the vehicle (NO in S10), whereas the processing proceeds to S20 if it is determined that one of the passenger doors is opened from inside the vehicle (YES in S10). Specifically, a door opening/closing switch 33 detects that one of the passenger doors is opened, where the passenger door is determined to be opened from inside the vehicle when it is detected that a door lock of the passenger door being opened is unlocked by an operation on an interior switch 34 provided on the passenger door.

Upon determining that the passenger door is opened from inside the vehicle, the processing proceeds to S20 and determines whether a passenger is left in the back seat 7 of the vehicle at the time all the passenger doors are locked in parking the vehicle. The present theft notification processing is completed if a passenger is left in the back seat 7 of the vehicle (YES in S20), whereas the processing proceeds to S30 if no passenger is left in the back seat 7 of the vehicle (NO in S20). Specifically, when the person detection flag is set, it is determined that a passenger is left in the back seat 7 of the vehicle at the time when all the passenger doors are locked in parking the vehicle.

Upon determining that no passenger is left in the back seat 7 of the vehicle, the processing proceeds to S30 and provides a theft notification, and then completes the theft notification processing. Specifically, the theft notification is provided by generating a warning sound toward the outside of the vehicle by using a speaker 62.

[2-3. Effect]

According to the second embodiment detailed above, the following effect can be obtained in addition to the effects [1A], [1B], and [1D] of the first embodiment described above.

[2A] If one of the passenger doors is opened from inside the vehicle after it is determined that no passenger is left in the vehicle at the time when all the passenger doors are locked in parking the vehicle (NO in S20), the warning sound is generated assuming that a suspicious person is present in the vehicle without being noticed by the passenger. The reason for generating the warning sound is to notify the outside of the vehicle of the presence of the suspicious person and to prevent the suspicious person from stealing the vehicle.

If it is determined that a passenger is left in the vehicle at the time when all the passenger doors are locked in parking the vehicle (YES in S20), the warning sound is not generated even when one of the passenger doors is thereafter opened as it is assumed that the passenger door is opened by the passenger. It is detected whether a passenger is left in the vehicle on the basis of a difference between the intensity of the detection transmission wave transmitted from a detection transmission unit 20 and the intensity of the detection transmission wave received by a vehicular receiver 13.

It is thus possible to prevent the generation of an unnecessary warning sound while the theft notification processing is being executed.

3. Third Embodiment

[3-1. Configuration]

Since the basic configuration of a third embodiment is similar to that of the first embodiment, a configuration different from the first embodiment will mainly be described while omitting a description of the configuration common to both embodiments.

Figure 10:
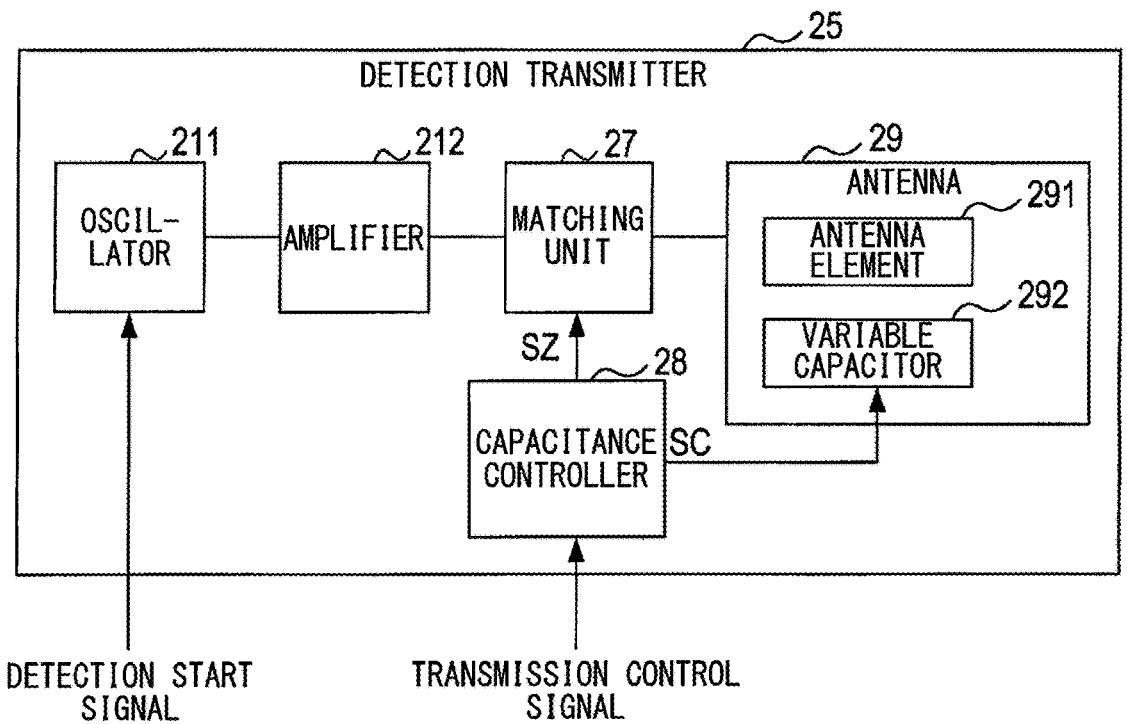
FIG. 10 is a block diagram illustrating the configuration of a detection transmission unit according to a third embodiment.

The third embodiment is different from the first embodiment in that the detection transmission unit 20 of the first embodiment is replaced with a detection transmission unit 25 illustrated in FIG. 10. That is, the first embodiment changes the directivity and a polarization state of the detection transmission wave of the detection transmission antenna 23 in the detection transmission unit 20, whereas the present embodiment changes a polarization state of a transmission detection wave transmitted from the detection transmission unit 25.

Figure 11:
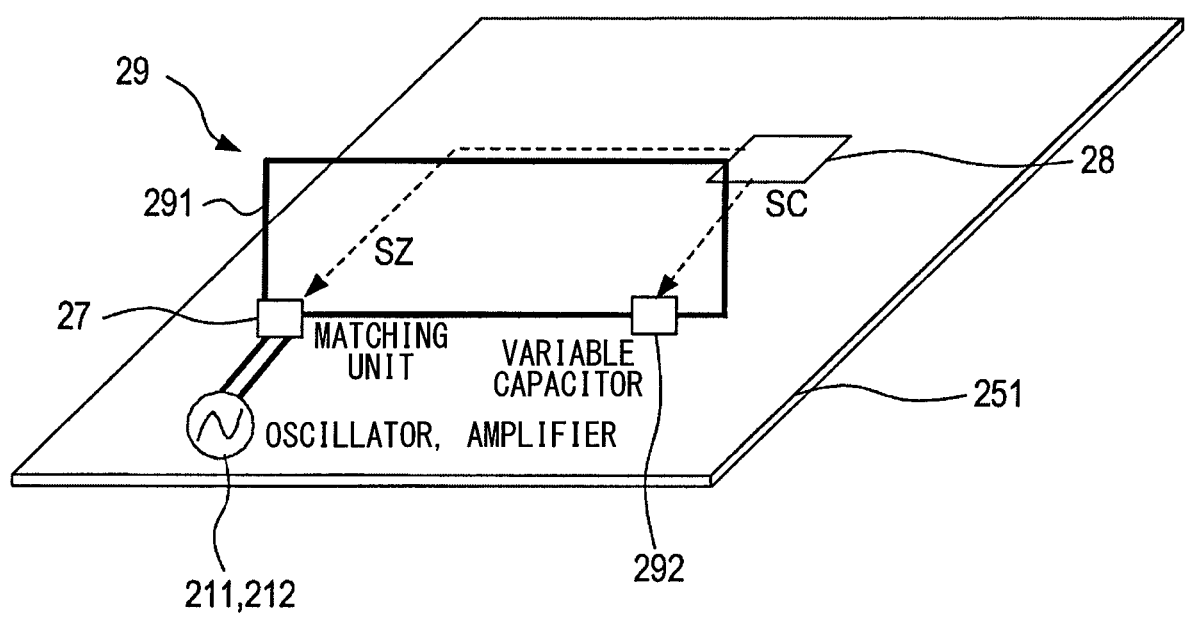
FIG. 11 is a schematic diagram illustrating the configuration of the detection transmission unit according to the third embodiment.

As illustrated in FIG. 10, the detection transmission unit 25 includes an oscillator 211, an amplifier 212, a matching unit 27, a capacitance controller 28, and a detection transmission antenna 29. The detection transmission unit 25 is formed by using a circuit board 251 as illustrated in an example of FIG. 11.

Returning to FIG. 10, the description will be continued. The matching unit 27 is an impedance matching circuit provided between the amplifier 212 and the detection transmission antenna 29. The matching unit 27 is configured to vary the impedance according to an impedance control signal SZ from the capacitance controller 28.

The detection transmission antenna 29 includes an antenna element 291 capable of forming a closed loop antenna, and a variable capacitor 292 provided on the path of the closed loop of the antenna element 291. The variable capacitor 292 is an element that can vary its capacitance according to a capacitance control signal, where a PIN diode is used as an example of the variable capacitor 292 in the present embodiment.

The capacitance controller 28 generates the capacitance control signal according to a transmission control signal from a control ECU 50 and supplies the signal to the detection transmission antenna 29, and at the same time generates the impedance control signal and supplies the signal to the matching unit 27. The capacitance control signal is generated so as to vary the capacitance of the variable capacitor 292 in response to the transmission control signal. The impedance control signal is generated so as to adjust the matching unit 27 such that a current flows efficiently to the antenna element 291 when the capacitance of the variable capacitor 292 is varied by the capacitance control signal.

According to the transmission control signal from the control ECU 50, the variable capacitor 292 in the antenna element 291 of the detection transmission antenna 29 can be short-circuited when the impedance is low, and the variable capacitor 292 in the antenna element 291 can be disconnected when the impedance is high. That is, the antenna element 291 is changed from a closed loop state to an open loop state according to the transmission control signal output from the control ECU 50, thereby allowing a change in the polarization state of the detection transmission antenna 29.

[3-2. Processing]

Figure 5:
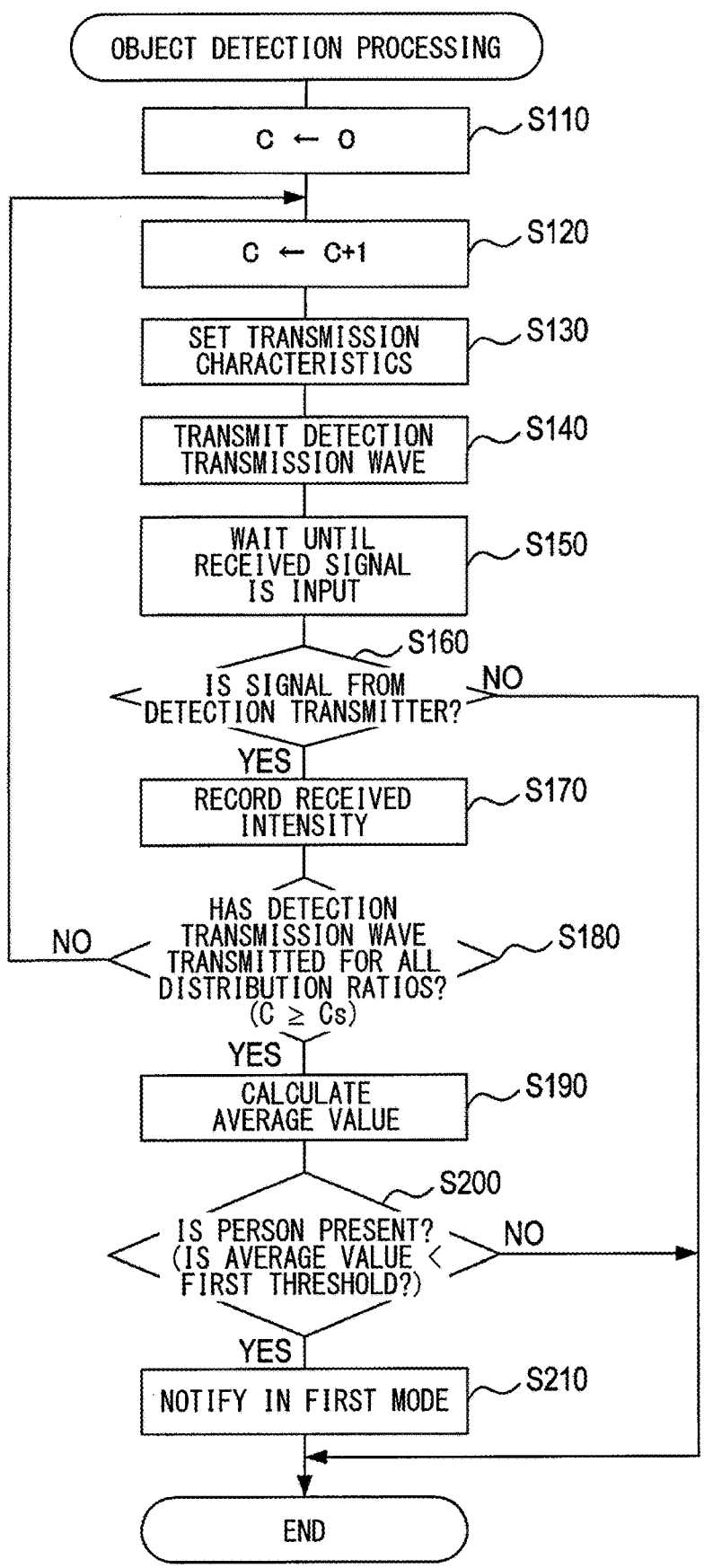
FIG. 5 is a flowchart of object detection processing.

The control ECU 50 of the present embodiment executes processing similar to the object detection processing illustrated in FIG. 5, except for the processing executed in S130 which is different from the first embodiment.

In S130, the control ECU 50 of the present embodiment sets a transmission characteristic when the detection transmission wave is transmitted by the detection transmission antenna 29 (the antenna element 291). As an example, the present embodiment outputs, as the transmission control signal, a signal that changes the impedance of the variable capacitor 292 in the detection transmission unit 25 from a low impedance value to a high impedance value as the value of a counter C changes from a small value to a large value.

[3-3. Effect]

According to the third embodiment detailed above, the following effect can be obtained in addition to the effects [1A] to [1D] of the first embodiment described above.

[3A] The detection transmission waves in different polarization states can be transmitted by one antenna (the detection transmission antenna 29), whereby the detection transmission unit 25 can be configured simply. In the third embodiment, the detection transmission unit 25 corresponds to an example of a transmitter, and the detection transmission antenna 29 corresponds to an example of a detection antenna.

4. Other Embodiment

Although the embodiments of the present disclosure have been described, it is needless to say that the present disclosure can adopt various forms in addition to the above-described embodiments.

[4A] In the above-described embodiments, the detection transmission waves is transmitted by changing the transmission characteristics of the detection transmission antennas 23 and 29 among the plurality of types to determine the presence or absence of a person on the basis of the average value of the reception intensities of the waves, but any configuration may be employed as long as the presence or absence of a person can be determined on the basis of the plurality of reception intensities. The presence or absence of a person may be determined on the basis of a maximum value of the reception intensities, for example. In this case, the processing in S190 of the flowchart illustrated in FIG. 5 may be replaced with processing of detecting the maximum value of the reception intensities, and the processing in S200 may be replaced with processing of determining that a person is present when the maximum value being detected is less than a predetermined threshold (a second threshold). An effect similar to that of the above-described embodiments can be obtained as a result.

[4B] In the above-described embodiments, the detection transmission antenna 23 is taken as an example of an antenna for which the polarization state and the directivity as the transmission characteristics can be changed. The above-described embodiments also use the detection transmission antenna 29 as an example of an antenna for which the polarization state as the transmission characteristic can be changed, but the antenna transmitting the detection transmission wave is not limited to these antennas. For example, a phased array antenna may be used as an antenna for which the directivity can be changed, or a dipole antenna having a rotating structure may be used as an antenna for which the polarization state can be changed. Alternatively, a circularly polarized antenna may be used.

[4C] In the above-described embodiments, a person in the back seat 7 of the vehicle is detected. However, an object to be detected is not limited to a person but may be an item different from the person in the back seat 7 of the vehicle such as baggage and the like in the back seat 7. Absorption of radio waves when the baggage and the like are to be detected is smaller than when a person is to be detected. Accordingly, when the baggage and the like are to be detected, the presence or absence of the baggage may be determined on the basis of a threshold larger than the threshold (first threshold or second threshold) used when a person is detected. It is then possible to notify the outside of the vehicle that a certain item other than a person is left in the vehicle. A notification mode may be set differently between when a person is detected and when baggage or the like is detected. This allows one to identify, from outside the vehicle, whether an object left in the vehicle is a person or an item different from a person on the basis of the notification mode.

[4D] In the above-described embodiments, the transmission wave transmitted from the electronic key 2 and the detection transmission wave transmitted from the detection transmission unit 20 are in the similar frequency band (UHF band). It is thus determined, when the authentication code is not included in received data, that the received signal including the received data is transmitted from the detection transmission unit 20 (YES in S160). However, the determination on whether the received signal is the detection transmission wave may be made in another way. For example, the data length of the data transmitted from the detection transmission unit 20 may be set to a length different from the data length of the data transmitted from the electronic key 2 (such as a length longer than the data length of the electronic key 2). It may then be determined whether the received signal including the received data is transmitted from the detection transmission unit 20 on the basis of the data length of the received data.

[4E] The transmission frequency of the transmission signal from the electronic key 2 and the frequency of the detection transmission wave from the detection transmission unit 20 may be set to different frequencies to thus determine from which of the electronic key 2 and the detection transmission unit 20 the received signal is transmitted, on the basis of the different frequencies.

[4F] In the above-described embodiments, the frequency of the detection transmission wave transmitted from the detection transmission unit 20 is set to a predetermined frequency in the UHF band, but may be set to a different frequency. The frequency of the detection transmission wave may be set to a frequency in any frequency band (such as a frequency in an industry-science-medical (ISM) band).

[4G] In the above-described embodiments, the warning is issued to the outside of the vehicle by using the speaker 62 and the hazard lamp 63, but may be issued to the outside of the vehicle by using another device. It is also possible to use the hazard lamp 63 to notify that a person is detected, or use the speaker 62 to notify that an item different from a person is detected.

[4H] In the above-described embodiments, the presence of an object in the back seat 7 of the vehicle is detected, but the present invention is not limited to the embodiments. The presence of an object in the passenger seat may be detected, for example.

[4I] In the above-described embodiments, the vehicular receiver 13, which is used to communicate with the electronic key 2 in the communication system 1, is used as a device that receives the detection transmission wave. However, the vehicular device 3 may include a device for receiving the detection transmission wave separately from the vehicular receiver 13.

[4J] The above-described embodiments include the device (the detection transmission unit 20) that transmits the detection transmission wave used to detect the presence of a certain object in the vehicle, and the device (the vehicular receiver 13) that receives the detection transmission wave. The present invention is not limited to the above-described embodiments. The vehicular device 3 may include a plurality of each of the device that transmits the detection transmission wave and the device that receives the detection transmission wave.

[4K] The function of one component in the above-described embodiments may be distributed as a plurality of components, or the functions of a plurality of components may be integrated into one component. Alternatively, at least a part of the configuration of the above-described embodiment may be replaced with a known configuration having a similar function. A part of the configuration of the above-described embodiments may also be omitted as long as the difficulty can be solved. Still alternatively, at least a part of the configuration of the above-described embodiments may be added to or replaced with the configuration of another one of the above-described embodiments. Note that all aspects of the technical concept specified from the language described in claims are embodiments of the present disclosure.

[4L] The present disclosure can be carried out in various forms such as a program that controls the control ECU 50 to function, a medium that stores the program, and an object detection method in addition to the communication system 1, the vehicular device 3, and the control ECU 50 described above.

It is noted that a flowchart or the processing of the flowchart in the present application includes sections (also referred to as steps), each of which is represented, for instance, as S10. Further, each section can be divided into several sub-sections while several sections can be combined into a single section. Furthermore, each of thus configured sections can be also referred to as a device, module, or means.

While the present disclosure has been described with reference to embodiments thereof, it is to be understood that the disclosure is not limited to the embodiments and constructions. The present disclosure is intended to cover various modification and equivalent arrangements. In addition, while the various combinations and configurations, other combinations and configurations, including more, less or only a single element, are also within the spirit and scope of the present disclosure.

What is claimed is:

1. An object detection apparatus mounted to a vehicle and detecting a predetermined object between a radio wave transmission end and a radio wave reception end, the object detection apparatus comprising:
    a transmitter configured to transmit a radio wave, which has a predetermined intensity, at the radio wave transmission end;
    a receiver configured to receive the radio wave, which is configured to be transmitted when the radio wave is transmitted from the transmitter, at the radio wave reception end; and
    a microcomputer configured to
        set a transmission scheme of the transmitter to a plurality of different transmission characteristics,
        control the transmitter to transmit the radio wave with the transmission scheme having the plurality of different transmission characteristics, in response to setting the transmission scheme, and
        detect a presence of the object located at a position inside the vehicle, based on a detected reception intensity indicating a respective radio wave reception intensity received by the receiver, the object blocking the radio wave having the plurality of different transmission characteristics transmitted from the transmitter to the receiver at the position inside the vehicle.

2. The object detection apparatus according to claim 1, wherein
    the transmitter includes a transmission antenna, and wherein
    the microcomputer is further configured to change a directivity of the transmission antenna as one of the plurality of transmission characteristics.

3. The object detection apparatus according to claim 1, wherein the microcomputer is further configured to change a polarization state of the radio wave transmitted from the transmitter as another one of the plurality of transmission characteristics.

4. The object detection apparatus according to claim 1, wherein the microcomputer is further configured to detect the presence of the object when an average value of the detected reception intensity is less than a predetermined threshold.

5. The object detection apparatus according to claim 1, wherein the the microcomputer is further configured to detect the presence of the object when a maximum value of the detected reception intensity is less than a predetermined threshold.

6. The object detection apparatus according to claim 1, wherein the microcomputer is further configured to output a notification to an outside of the vehicle notifying that the object is present inside the vehicle, in response to the microcomputer detecting the presence of the object.

7. The object detection apparatus according to claim 1, wherein
the microcomputer is further configured to determine whether the object is present at a position inside the vehicle between the transmitter and the receiver based on an absorption of the transmitted radio wave by the object.

8. The object detection apparatus according to claim 7, wherein
the object is a passenger inside the vehicle.

9. The object detection apparatus according to claim 1, wherein
the transmitter includes a first transmission antenna and a second transmission antenna, and wherein
one of the plurality of different transmission characteristics includes a plurality of distribution ratios when the first transmission antenna and the second transmission antenna send a radio wave.

10. The object detection apparatus according to claim 9, wherein
each of the plurality of distribution ratios is a ratio between a transmission power of the first transmission antenna and a transmission power of the second transmission antenna.

11. The object detection apparatus according to claim 9, wherein
the microcomputer is further configured to set the transmitter to one of the plurality of distribution ratios.

* * * * *